US010130782B2

(12) United States Patent
Ho

(10) Patent No.: US 10,130,782 B2
(45) Date of Patent: Nov. 20, 2018

(54) PARAMETRIC APPROACH TO MASK CUSTOMIZATION

(71) Applicant: KONINKLIJKE PHILIPS N.V., Eindhoven (NL)

(72) Inventor: Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1025 days.

(21) Appl. No.: 14/362,461

(22) PCT Filed: Dec. 4, 2012

(86) PCT No.: PCT/IB2012/056928
§ 371 (c)(1),
(2) Date: Jun. 3, 2014

(87) PCT Pub. No.: WO2013/088293
PCT Pub. Date: Jun. 20, 2013

(65) Prior Publication Data
US 2014/0352134 A1    Dec. 4, 2014

Related U.S. Application Data

(60) Provisional application No. 61/569,997, filed on Dec. 13, 2011.

(51) Int. Cl.
*G06F 19/00* (2018.01)
*G06G 7/50* (2006.01)
(Continued)

(52) U.S. Cl.
CPC ........ *A61M 16/0616* (2014.02); *A61M 16/06* (2013.01); *A61M 16/0611* (2014.02);
(Continued)

(58) Field of Classification Search
CPC .......... A61M 16/0616; A61M 16/0633; A61M 16/0611; A61M 16/06; A61M 2016/0661; Y10T 29/49
(Continued)

(56) References Cited

U.S. PATENT DOCUMENTS 5,009,626 A * 4/1991 Katz ........................ A63H 3/02
156/59
6,487,304 B1   11/2002 Szeliski
(Continued)

FOREIGN PATENT DOCUMENTS

DE    102005042911 A1    2/2007
DE    202010011334 U1    10/2010
(Continued)

OTHER PUBLICATIONS

Young, J.W., "Selected Facial Measurements of Children for Oxygen-Mask Design", Federal Aviation Agency, Office of Aviation Medicine, Apr. 1966, pp. 1-11.

*Primary Examiner* — Robert A Cassity
*Assistant Examiner* — Gary Collins
(74) *Attorney, Agent, or Firm* — Michael W. Haas

(57) ABSTRACT

A method of providing a semi-custom patient interface device is disclosed. The semi-custom patient interface device is based upon both generic facial parameters and the facial parameters of a specific individual.

8 Claims, 10 Drawing Sheets

(51) Int. Cl.
*A61M 16/06* (2006.01)
*A61F 11/00* (2006.01)

(52) U.S. Cl.
CPC ............... *A61M 16/0633* (2014.02); *A61M 2016/0661* (2013.01); *Y10T 29/49* (2015.01)

(58) Field of Classification Search
USPC ............ 700/98; 128/204.18, 203.29, 205.25, 128/857; 703/11
See application file for complete search history.

(56) References Cited

U.S. PATENT DOCUMENTS

| | | | |
|---|---|---|---|
| 8,254,637 B2* | 8/2012 | Abourizk | A61M 16/06 356/601 |
| 2003/0196655 A1* | 10/2003 | Ging | A61M 16/06 128/201.22 |
| 2006/0023228 A1* | 2/2006 | Geng | A61B 5/411 356/601 |
| 2008/0006273 A1 | 1/2008 | Thornton | |
| 2008/0078396 A1 | 4/2008 | Janbakhsh | |
| 2010/0111370 A1 | 5/2010 | Black | |
| 2010/0310175 A1 | 12/2010 | Holt | |
| 2011/0088698 A1 | 4/2011 | Barnett | |
| 2013/0070973 A1* | 3/2013 | Saito | G06K 9/036 382/118 |

FOREIGN PATENT DOCUMENTS

| | | |
|---|---|---|
| JP | 2010131091 A | 6/2010 |
| TW | 200520811 A | 7/2005 |
| WO | WO2011049548 A1 | 4/2011 |

\* cited by examiner

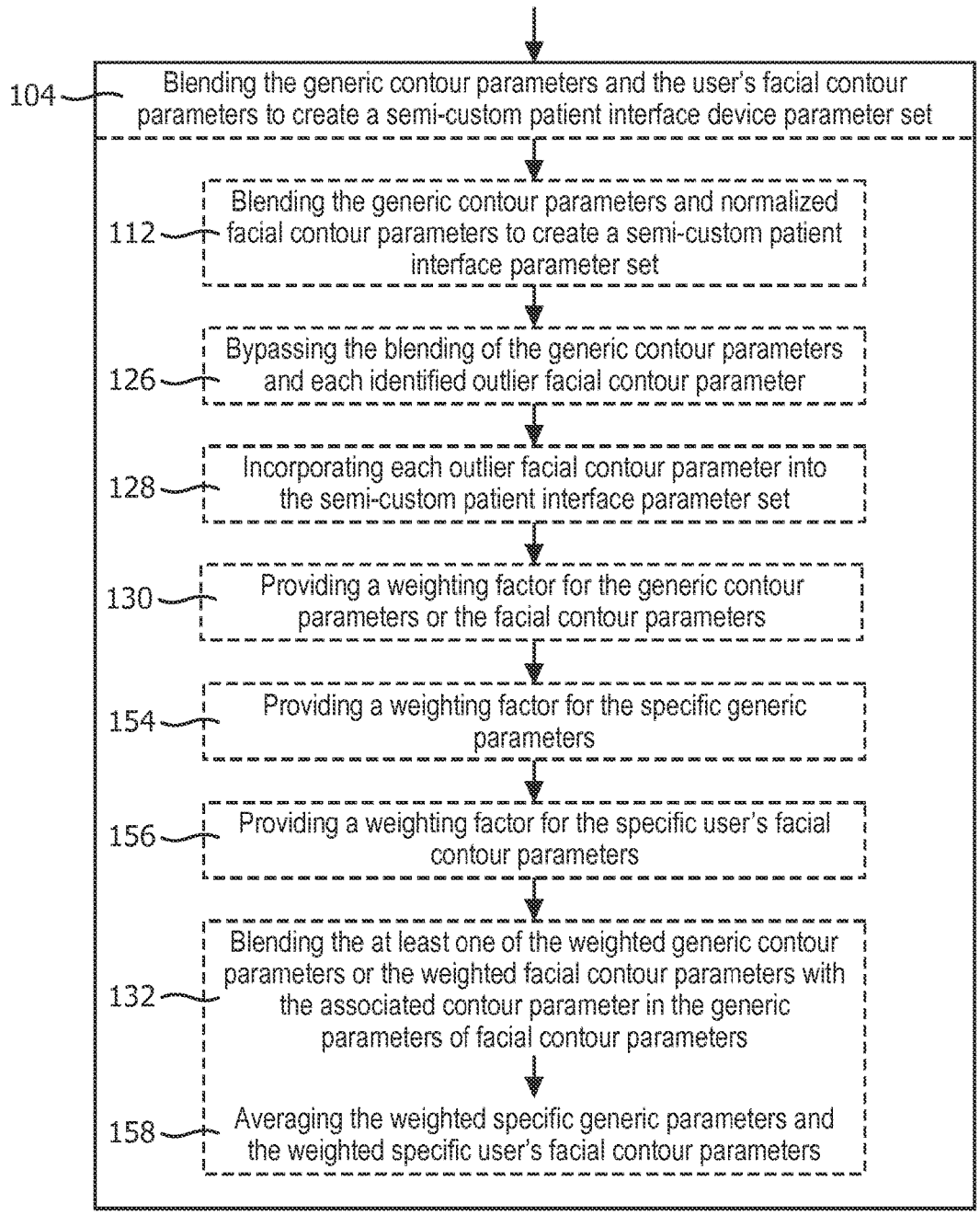
FIG. 7A (Continue)

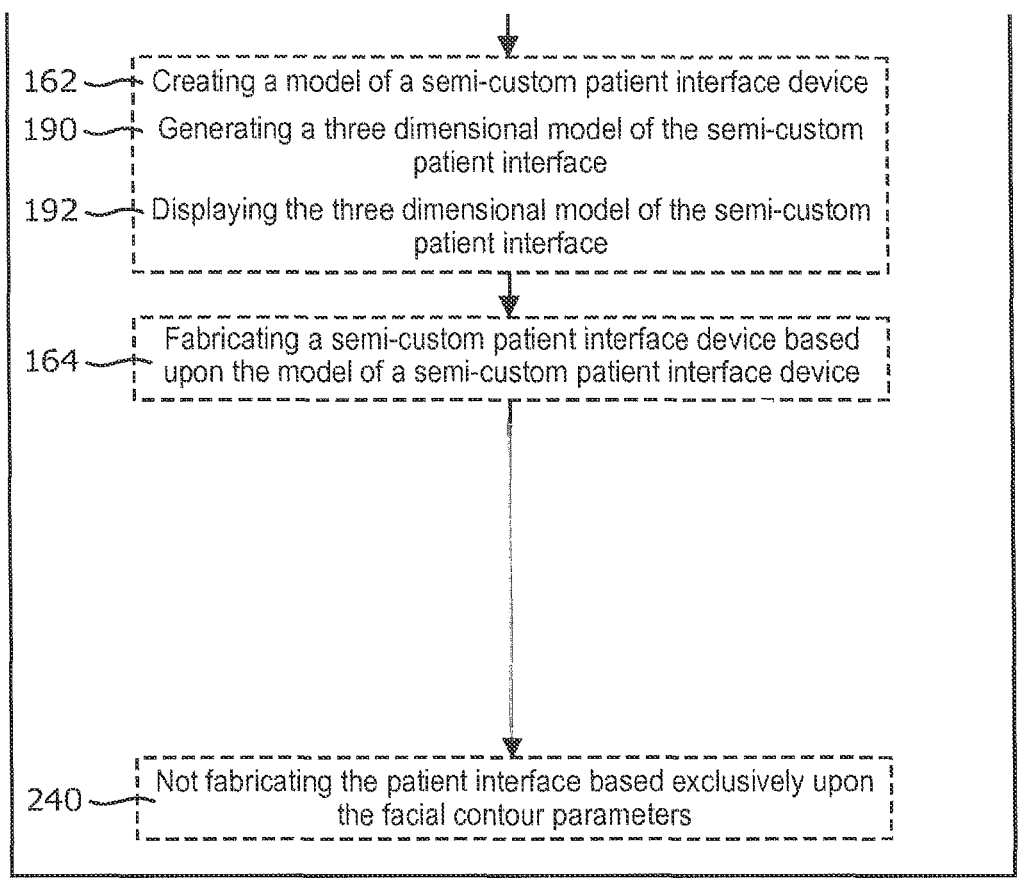
FIG. 7B (Continue)

PARAMETRIC APPROACH TO MASK CUSTOMIZATION

CROSS-REFERENCE TO RELATED APPLICATIONS

This patent application claims the priority benefit under 35 U.S.C. § 371 of international patent application no. PCT/IB2012/056928, filed Dec. 13, 2012, which claims the priority benefit under 35 U.S.C. § 119(e) of U.S. Provisional Application No. 61/569,997 filed on Dec. 13, 2011, the contents of which are herein incorporated by reference.

BACKGROUND OF THE INVENTION

1. Field of the Invention

The present invention pertains to respiratory patient interface devices and, in particular, to a method of providing a semi-custom patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle, and auto-titrating pressures, wherein the pressure varies with the condition of the patient (e.g., snoring, apneas, hypopneas, etc.) or with the condition of the therapy system (e.g., large leaks). Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion that rests beneath the patient's nose (such as a "pillows" style nasal cushion having nasal prongs that are received within the patient's nares or a "cradle" style nasal cushion that rests beneath and covers the patient's nares), a nasal/oral mask that covers the nose and mouth, or a total face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient.

The mask component of a patient interface device has a certain amount of leak designed into it for allowing exhaled gas to leave the system. This designed-in leak is known as intentional or exhalation leak and is the leak needed to remove exhaled gases from the system. Residual leak is the leak that is not designed into the mask but is still present, often due to a poor fit. Traditionally, the dimensions and contours of the patient interface device were based on a generic model. That is, the patient interface device was sized and shaped to fit on a user with broadly average facial features. One advantage to such generic patient interface device is that by being structured to fit onto a variety of faces, the generic patient interface device would also provide an adequate fit for a single user regardless of that user's expression. While this construction allows for mass production of patient interface devices, the patient interface devices typically did not fit any one person precisely. When the patient interface device does not fit a user precisely, there is an increased chance that the patient interface device will allow fluid, typically pressurized air, to leak. Further, a patient interface device that does not fit a user correctly may be uncomfortable. There have been at least two attempts to overcome these problems.

Initially, patient interface devices were adapted to multiple generic models. That is, there was a generic female patient interface device, a generic child patient interface device, etc. While these patient interface devices allowed for a better fit than the broadly generic model, the problems persisted because the patient interface devices still did not fit any one person precisely. As three-dimensional scanning techniques improved and custom fabrication became less expensive, custom patient interface devices could be fabricated. Ironically, custom patient interface devices suffered from some of the same problems as the patient interface devices that were based on a generic model, i.e. a custom patient interface device often provided a bad fit. This was likely because the three-dimensional scanning techniques typically provided a snapshot of the user's face at a single moment, i.e. with a single facial expression. This, in turn, created at least two similar problems when creating custom patient interface devices.

First, if the user had a particular facial expression, such as a smile or frown, when the scan was being made, the custom patient interface device would be structured to fit the user when the user had the same expression. Thus, users were typically advised to maintain a "neutral expression" during the scan. The second problem was, even if a user maintained a neutral expression during the scan, the resulting parameters that were measured were based exclusively on the user's face at a single moment in time. While a custom patient interface device based on a scan of a neutral expression typically fit better in most instances than would a custom patient interface device based on a scan of a particular expression, the custom patient interface device was still structured to fit the user's single expression. That is, if during use of the custom patient interface device, the user changed their expression from the neutral expression, the custom measurements were no longer accurate and the custom patient interface device did not provide a precise fit.

Thus, a generic patient interface device provided a fit that was generally acceptable to a variety of face sizes and shapes, but not precise to any specific one. Conversely, a custom patient interface device provided a fit that was precise for a user so long as the user's face maintained the expression that was captured in the scan upon which the custom patient interface device was based.

SUMMARY OF THE INVENTION

One embodiment of the present invention provides a method of providing a semi-custom patient interface device that includes the steps of providing a patient interface model having a set of generic contour parameters, acquiring a set of user's facial contour parameters, blending the generic contour parameters and the user's facial contour parameters to create a semi-custom patient interface device parameter set, and fabricating the semi-custom patient interface device based upon the semi-custom patient interface device parameter set.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
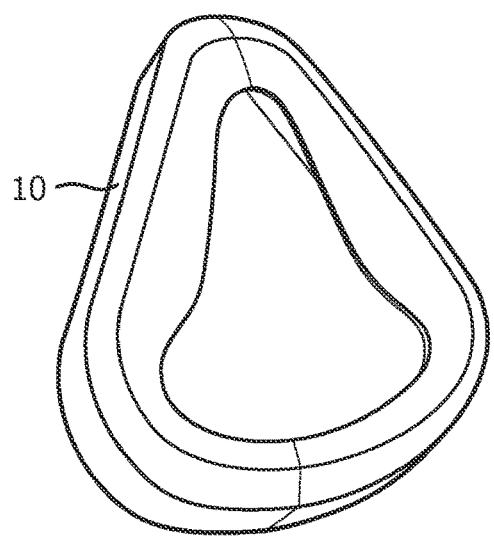
FIG. 1 is an isometric view of a generic patient interface device.

As used herein, the singular form of "a", "an", and "the" include plural references unless the context clearly dictates otherwise. As used herein, the statement that two or more parts or components are "coupled shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall means that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, a "semi-custom patient interface device" is not based exclusively on anyone person's facial features, i.e. parameters. Nor is a "semi-custom patient interface device" based exclusively on generic facial features or parameters. A "semi-custom patient interface device" must be based upon a specific person's facial features or parameters combined with generic facial features or parameters.

Figure 2:
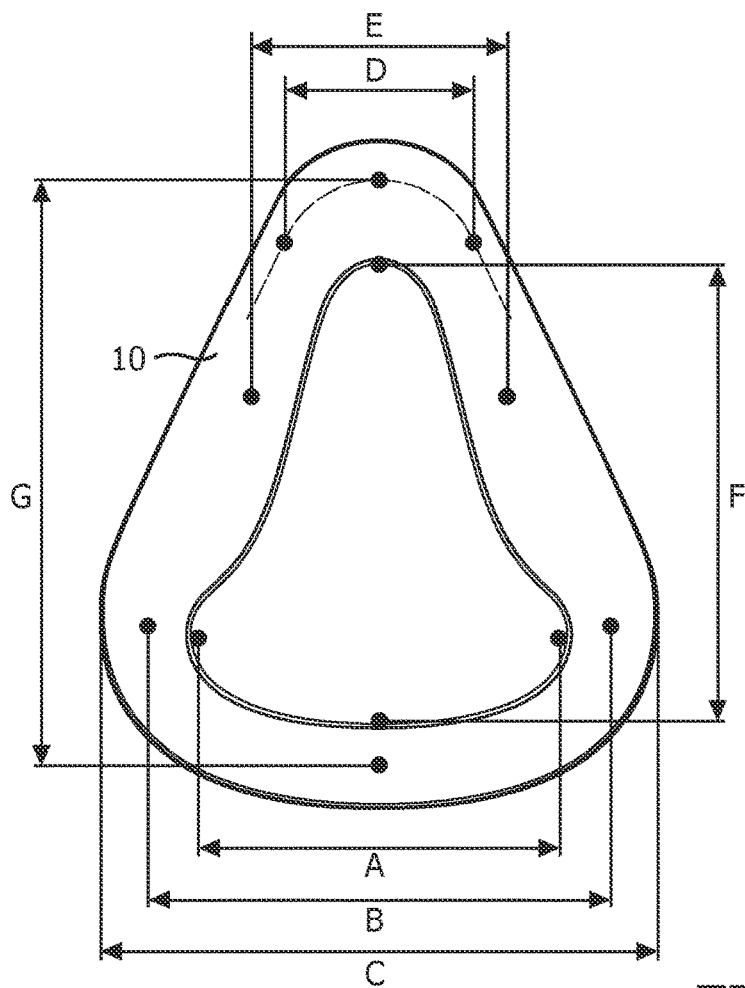
FIG. 2 is a back view of a patient interface device.
Figure 3:
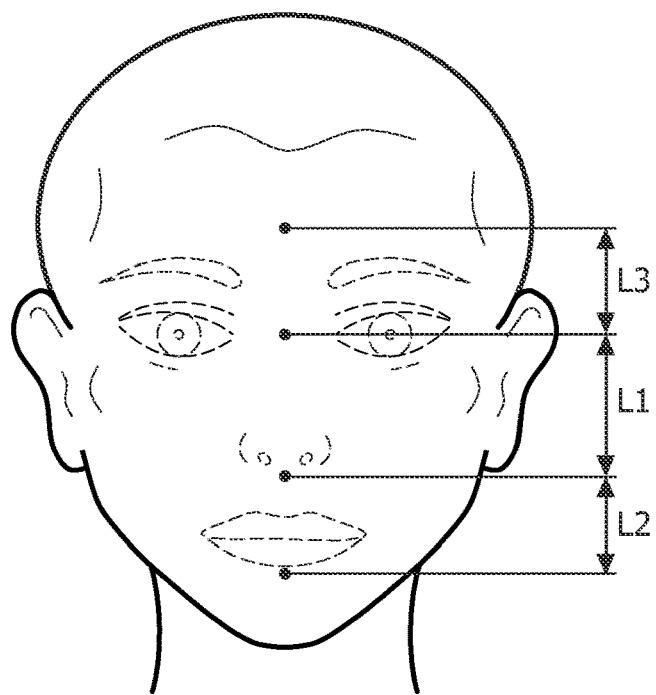
FIG. 3 is a front view of a human face indicating selected dimensions.

FIGS. 1 and 2 show a patient interface device 10 according to one exemplary embodiment including the inner side of patient interface device 10, i.e. the side that contacts the user's face. As shown in FIG. 2, patient interface device 10 has a number of exemplary identifiable dimensions including Opening Width (A), Tangent Width around Mouth (B), Overall Width (C), Tangent Width between the Sides of the Nose (D), Cheek Width (E), Opening Height (F), and Tangent Height (G). There are other identifiable patient interface device 10 dimensions that may be customized, or semi-customized.

In a generic patient interface device 10, the identifiable dimensions are based upon a set of generic contour parameters representing a generic face. The generic contour parameters are fixed, but there may be two or more sets of generic contour parameters wherein each set of generic contour parameters represents an identifiable group of humans. That is, for example, there could be a set of "female" generic contour parameters or a set of "child" generic contour parameters. While this is understood, the remaining discussion shall refer to a single set of exemplary generic contour parameters.

Prior to fabrication of a physical generic patient interface device 10, there is a generic model for a generic face, typically a mathematical or computer model (i.e. not a physical model), having the generic contour parameters for the generic face incorporated therein. As shown on FIGS. 3-5B, in the exemplary embodiment, these generic contour parameters include:

| | |
|---|---|
| W1 | Mouth Width |
| W2 | Nose Width |
| W3 | Eye Spacing Width |
| L1 | Nose Length |
| L2 | Base Of Nose To Base Of Mouth |
| L3 | Bridge Of Nose To Forehead |
| D1 | Depth Of Nose Bridge |
| D2 | Right, First Depth To The Side Of The Nose |
| D3 | Right, First Depth To The Base Of The Nose |
| D4 | Right, First Depth To The Corner Of The Mouth |
| D5 | Depth To The Base Of The Mouth |
| D6 | Left, Second Depth To The Corner Of The Mouth |
| D7 | Left, Second Depth To The Base Of The Nose |
| D8 | Left, Second Depth To The Side Of The Nose |
| D9 | Depth To The Forehead |

These generic contour parameters are typically based on a study of multiple faces of people of different ages, genders, weights, heights, and race. As can be seen, the parameters are represented by lines, i.e. data for a set of aligned points having coordinates. The lines have two end points. Typically, in a generic set of data, the two end points of a horizontal line are an equal distance from a central vertical axis. That is, the data representing a generic face also represents a substantially symmetrical face. Any "depth" parameter is measured from the tip of the nose toward the face. In an exemplary embodiment, the measurements are recorded as lengths measured in millimeters. As described in greater detail herein, in the exemplary embodiment, the dimensions of generic patient interface device 10 are fabricated based on the generic contour parameters. That is, the dimensions of patient interface device 10 are a function of the generic contour parameters. As a "parameter" is recorded as a set of data representing a line, or at least the end points of the line, the word "parameter" shall hereinafter mean the set of data or line represented thereby. Thus, "parameters" may be manipulated, blended, combined or otherwise altered as any set of data could be manipulated, blended, combined or altered.

Further, using any known scanning technique, such as, but not limited to laser scanning methods, sonic scanning methods, and imaging methods (e.g., 2D and/or 3D scanning or mapping), the user's facial contour parameters of a specific user may be acquired. This data is typically acquired as mathematical or computer data that is generated by a scanning device structured to provide electronic data as an output. This data is stored in an electronic format, e.g. on a hard drive, flash memory, etc, as is well known. The raw data may be enhanced manually. For example, a scanning device may capture an image of a face and determine a parameter, e.g., nose width. A technician may manually alter this data to be more accurate.

Thus, there are "generic contour parameters" which, as used herein, means a predetermined set of user's facial contour parameters based on an average human. There are also, "user's facial contour parameters" which, as used herein, means a set of user's facial contour parameters obtained from a specific user as described above. The scanned user's facial contour parameters shall be referred to collectively as the "user's facial contour parameters." Any specific user facial contour parameter shall be identified as the "user's _____ parameter," i.e., the blank in the phrase, "user's _____ parameter," may be filled in by one of the named parameters set forth in the chart above. For example, there is a "user's Mouth Width parameter," which is the Mouth Width of a specific person acquired, for example, by scanning the user's Mouth Width, a "user's Eye Spacing Width parameter," which is the Eye Spacing Width of a specific person acquired, for example, by scanning the user's Eye Spacing Width, etc.

Thus, the generic contour parameters and the user's facial contour parameters are sets of data having associated pairs of data subsets. That is, for each generic contour parameter there is an "associated" user's facial contour parameter. For example, the "Eye Spacing Width parameter" is the distance between the corners of the eyes. Thus, there is a "generic Eye Spacing Width parameter" that is "associated" with the "user's Eye Spacing Width parameter" in that both parameters refer to the measurement of the same physical features. It is understood that "associated" parameters may be blended, by averaging the two parameters. That is, the generic Mouth Width parameter may be blended with the user's Mouth Width parameter as they are "associated." Non-associated parameters, e.g. the "generic Nose Width parameter" and the "user's Bridge of Nose to Forehead parameter" cannot be combined as "associated" parameters.

Figure 6:
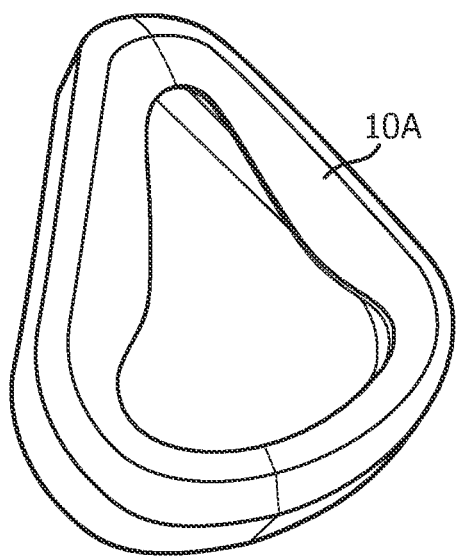
FIG. 6 is an isometric view of a semi-custom patient interface device.

The generic contour parameters and the user's facial contour parameters are blended to create a semi-custom patient interface device parameter set. That is, semi-custom patient interface device parameter set is a third set of parameters, which is a blending of the generic contour parameters and the user's facial contour parameters. As detailed below, the semi-custom patient interface device parameter set is used to fabricate semi-custom patient interface device 10A, as shown in FIG. 6. As is known, when sets of data having like subsets of data are combined, the resulting set of data has subsets corresponding to the original sets of data. As used herein, "blended" means that similar sets of data, i.e. data representing similar physical features, are combined. Broadly, or in one exemplary embodiment, the blending is simply an averaging the generic contour parameters and the user's facial contour parameters. Thus, if the generic contour parameter for Mouth Width indicated a length of 1.5 inches and a user's Mouth Width was 1.65 inches, the semi-custom patient interface device parameter set may indicate that the Mouth Width is 1.575 inches. Again, this is a broad example; the blending may, for example, account for a user having a mouth wherein the line representing Mouth Width is not a horizontal line.

In an exemplary embodiment, the blending of the generic contour parameters and the user's facial contour parameters may occur as follows. As noted above and in FIG. 4, there are at least three generally horizontal parameters; the Mouth Width (W1), the Nose Width (W2), and the Eye Spacing Width (W3). Accordingly, the generic mask has a generic Mouth Width (W1$_{gen}$), a generic Nose Width (W2$_{gen}$), and a generic Eye Spacing Width (W3$_{gen}$). Further, following a scan of the patient's face, or after acquiring the patient's parameters by any known method, the user's parameters, i.e. the user's Mouth Width (W1$_{user}$), the user's Nose Width (W2$_{user}$), and the user's Eye Spacing Width (W3$_{user}$) are acquired.

To blend the generic and the user parameters a scaling factor is established. For example, the scaling factor (SF) may be equal to the average of the ratio of the various width parameters. That is, $$SF = \frac{\left(\left(\frac{W1_{user}}{W1_{gen}}\right) + \left(\frac{W2_{user}}{W2_{gen}}\right) + \left(\frac{W3_{user}}{W3_{gen}}\right)\right)}{3}.$$

The generic parameters may then be modified by the scaling factor to establish the parameters for the semi-custom patient interface device 10A. That is, the semi-custom Mouth Width (W1$_{semi}$)=(W1$_{gen}$)*SF, the semi-custom Nose Width (W2$_{semi}$)=(W2$_{gen}$)*SF, and so forth.

The other parameters may be blended in a similar manner. That is, the ratios of two or more vertical parameters may be averaged to determine a vertical scaling factor and the ratios of two or more depth parameters may be averaged to determine a depth scaling factor. Further, selected parameters associated with one facial feature may be blended to determine a specific scaling factor. For example, the parameters for the Depth Of Nose Bridge (D1), Right, First Depth To The Side Of The Nose (D2), Right, First Depth To The Base Of The Nose (D3), Left, Second Depth To The Base Of The Nose (D7), and Left, Second Depth To The Side Of The Nose (D8) may be grouped as a "Nose Scaling Factor," or, the parameters Right, First Depth To The Corner Of The Mouth (D4), Depth To The Base Of The Mouth (D5), and Left, Second Depth To The Corner Of The Mouth (D6) may be grouped as a "Mouth Scaling Factor." Such localized scaling factors would typically be applied to the associated generic parameters during the step of blending.

This exemplary embodiment demonstrates one relatively simple method of blending the parameters; the method may use other equations and algorithms to accomplish the blending. For example, in another exemplary embodiment, the scaling factor may be enhanced by a racial modifier. That is, it is known that certain races may tend to have a wide nose or a thin nose. A racial modifier may be incorporated into the equation to account for such differences. For example, if the patient is of a race that tends to have a wider nose, the scaling factor may be determined by the equation $$SF = \frac{\left(\left(\frac{W1_{user}}{W1_{gen}}\right) + \left(\left(\frac{W2_{user}}{W2_{gen}}\right) * RM\right) + \left(\frac{W3_{user}}{W3_{gen}}\right)\right)}{3},$$

wherein the racial modifier (RM)=1.5. Again, these equations demonstrate one relatively simple method of blending the parameters; and the method may use other equations and algorithms to accomplish the blending.

Figure 4:
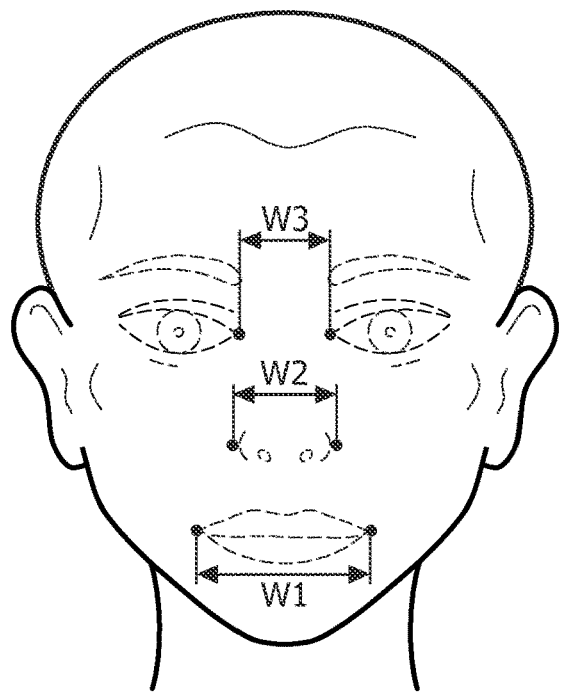
FIG. 4 is a front view of a human face indicating selected dimensions.
Figure 5B:
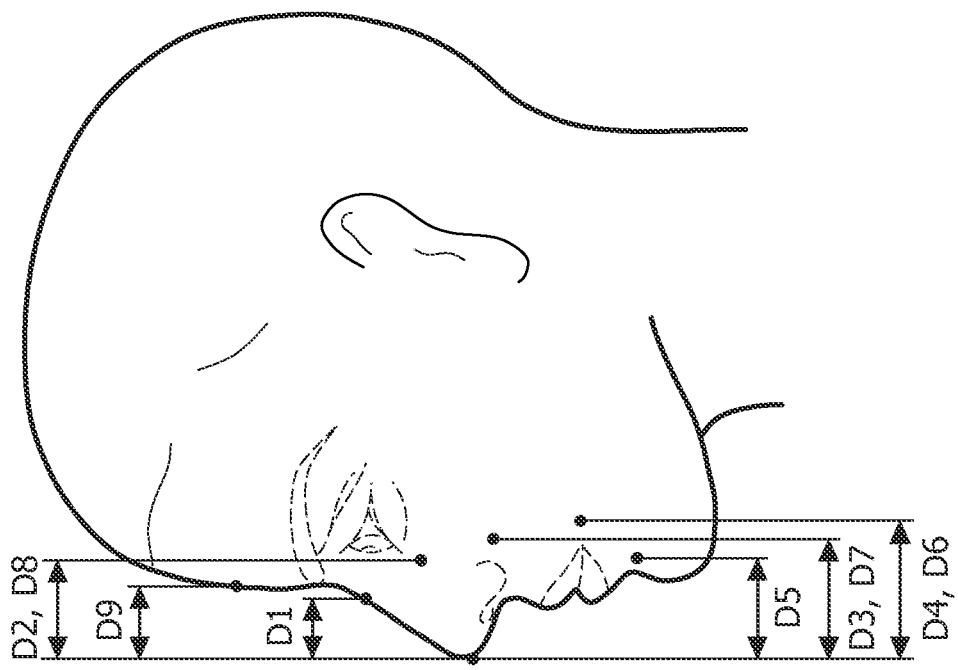
FIGS. 5A and 5B are a front view and a side view of a human face indicating selected dimensions.
Figure 5A:
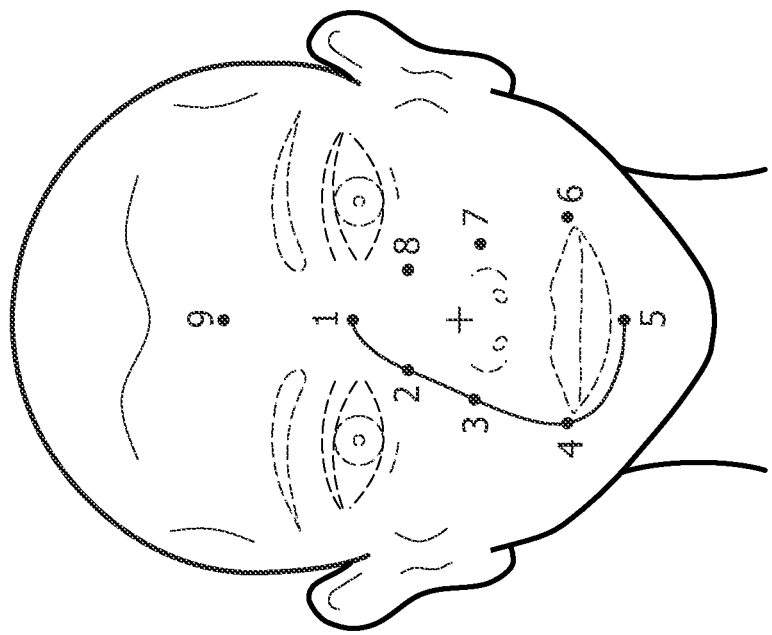

As noted above, scanning of a user's features may result in an atypical expression, e.g., the user is scanned while smirking (a smile favoring one side). Alternately, some user's may have asymmetrical faces. It is generally not desirable to incorporate asymmetrical parameters into semi-custom patient interface device 10A. The effects of such asymmetric parameters may be minimized by normalizing the user's facial contour parameters. The normalization may be accomplished by various methods such as "leveling" a line so as to be horizontal. That is, various parameters, e.g. Mouth Width, are generally horizontal lines, as shown in FIG. 4. If a user's face is slightly asymmetrical, the line representing the user's Mouth Width may not be horizontal. Such an asymmetrical parameter may be normalized by "leveling" the line, i.e. converting the line to be a substantially horizontal line while substantially maintaining the other characteristics of the line such as, but not limited to, total length.

In one embodiment, the horizontal user's facial contour parameters are made substantially symmetrical about a vertical axis. That is, a vertical axis is imposed, e.g. incorporated into the stored data, on the user's facial contour parameters. Any horizontally asymmetrical measurements may be identified by measuring the distance between vertical axis and the end points of a horizontal line representing a parameter. That is, the line representing a parameter is broken into segments disposed on either side of the vertical axis. If the segments of a line representing the parameter are not a substantially equal length, the parameter is normalized by converting the segments into segments with substantially the same length. Typically, this is accomplished by converting the lesser segment length to be equal to the greater segment length. Thus, it is typical to provide more room, i.e. a greater distance from the vertical axis, in semi-custom patient interface device 10A than a lesser distance. Symmetry may also be achieved by averaging the length of the two segments or by converting the greater segment length to be equal to the lesser segment length.

While it is typical to use normalized user's facial contour parameters, a user's specific features may be sufficiently asymmetrical that normalized user's facial contour parameters may not be desirable. An extreme asymmetry means that at least one facial contour parameter may be identified as an "outlier" user's facial contour parameter. When an "outlier" facial contour parameter is identified, the "outlier" user's facial contour parameter is not normalized. That is, the other user's facial contour parameters may be normalized, but the normalization of the "outlier" user's facial contour parameter is bypassed. Further, when this occurs, the "outlier" user's facial contour parameter is typically not blended with the generic contour parameters. That is, when an "outlier" user's facial contour parameter is identified, that parameter is typically incorporated into the semi-custom patient interface device parameter set.

Further, the blending of the generic contour parameters and the user's facial contour parameters may favor one set of parameters over the other. That is, because the contour parameters are structured as lines, the blending thereof may be easily accomplished by averaging the two parameters, i.e. the generic contour parameter and the associated user's facial contour parameter. There may, however, be a desire to favor one contour parameter over the other. This favoring may be performed for each contour parameter. For example, it may be determined that semi-custom patient interface device 10A provides a better seal and is more comfortable when the user's Mouth Width is used and the generic Nose Width is used. If the degree of favoritism is that extreme, the non-desired parameter may simply be ignored. Typically, however, the favoritism is more limited.

For a more limited favoritism, the contour parameters are "weighted." That is, one of either the generic contour parameters or the user's facial contour parameters is enhanced, or diminished, relative to the associated parameter prior to blending. For example, if the user's Mouth Width parameter is to be favored, the acquired Mouth Width parameter may be enhanced by a factor of 10%. Thus, when the generic Mouth Width parameter is blended with the enhanced user's Mouth Width parameter, the resulting blended Mouth Width parameter will be closer to the user's Mouth Width parameter than to the generic Mouth Width parameter. As used herein, once one parameter has been enhanced or diminished, all parameters, in both the generic contour parameters or the user's facial contour parameters are "weighted" parameters; the weighting may, however, be by a factor of 0%. That is, if the user's Mouth Width parameter is enhanced by a factor of 10% and all other parameters are not altered (enhanced by a factor of 0%), all the parameters in both the generic contour parameters or the user's facial contour parameters are "weighted" parameters.

A semi-custom patient interface device parameter set is created by blending the generic contour parameters and the user's facial contour parameters. It is understood that the generic contour parameters and the user's facial contour parameters are typically stored electronically and data manipulation is performed by a computer, or similar device, and that the resulting data is, typically, stored in an electronic format. It is understood, and as used herein, that the semi-custom patient interface device parameter set includes the "blended" contour parameters. That is, the semi-custom patient interface device parameter set having a blended contour parameters is inherent. Moreover, the parameters, i.e., subsets of data, within the semi-custom patient interface device parameter set correspond to the parameters within the generic contour parameters and the user's facial contour parameters. Thus, it is understood that the semi-custom patient interface device parameter set includes, for example, a blended Mouth Width parameter, a blended Nose Width parameter, and so forth.

As noted above, patient interface device 10 has identifiable dimensions including Opening Width, Tangent Width Around Mouth, Overall Width, Tangent Width Between the Sides of the Nose, Cheek Width, Opening Height, and, Tangent Height. Each of these identified dimensions may be influenced exclusively by one parameter or a combination of parameters in the semi-custom patient interface device parameter set. That is, there is a mathematical correlation between the blended contour parameters and the size, shape and contours of final semi-custom patient interface device 10A as manufactured. The equations that represent this correlation are hereinafter referred to as "functions." That is, as used herein, a "function" is an equation that converts at least one input of a blended parameter from the semi-custom patient interface device parameter set to a specific dimension on resulting semi-custom patient interface device 10A. That is, during fabrication, each identified dimension may be a "function" of one parameter or a combination of parameters in the semi-custom patient interface device parameter set. Thus, the blended parameters in the semi-custom patient interface device parameter set may be used to create a model of semi-custom patient interface device 10A. As before, it is understood that the calculations used to create this model are performed on a computer, or similar device, and the resulting model is electronically stored data, not a physical model.

Moreover, one or more parameters may have a greater or lesser effect on a selected dimension of semi-custom patient interface device 10A. Thus, it may be said that selected parameters have a primary or secondary effect on selected semi-custom patient interface device 10A dimensions. Because of this, any identifiable dimensions of semi-custom patient interface device 10A may be said to be determined as a primary function of selected blended parameters and well as a secondary function of other selected blended parameters.

The model of semi-custom patient interface device 10A may be converted into a physical semi-custom patient interface device 10A utilizing any known fabrication methods. Such adaptable fabrication methods are identified as "quick tool" methods and include, but are not limited to, quick mold using a Master Unit Die tool having a plurality of replaceable inserts having different dimensions and contours. Such inserts may be formed with Additive Manufacturing materials such as, but not limited to, a selective laser sintering metal or any composite structured to withstand the heat and pressure of the cushion forming process.

Figure 7A:
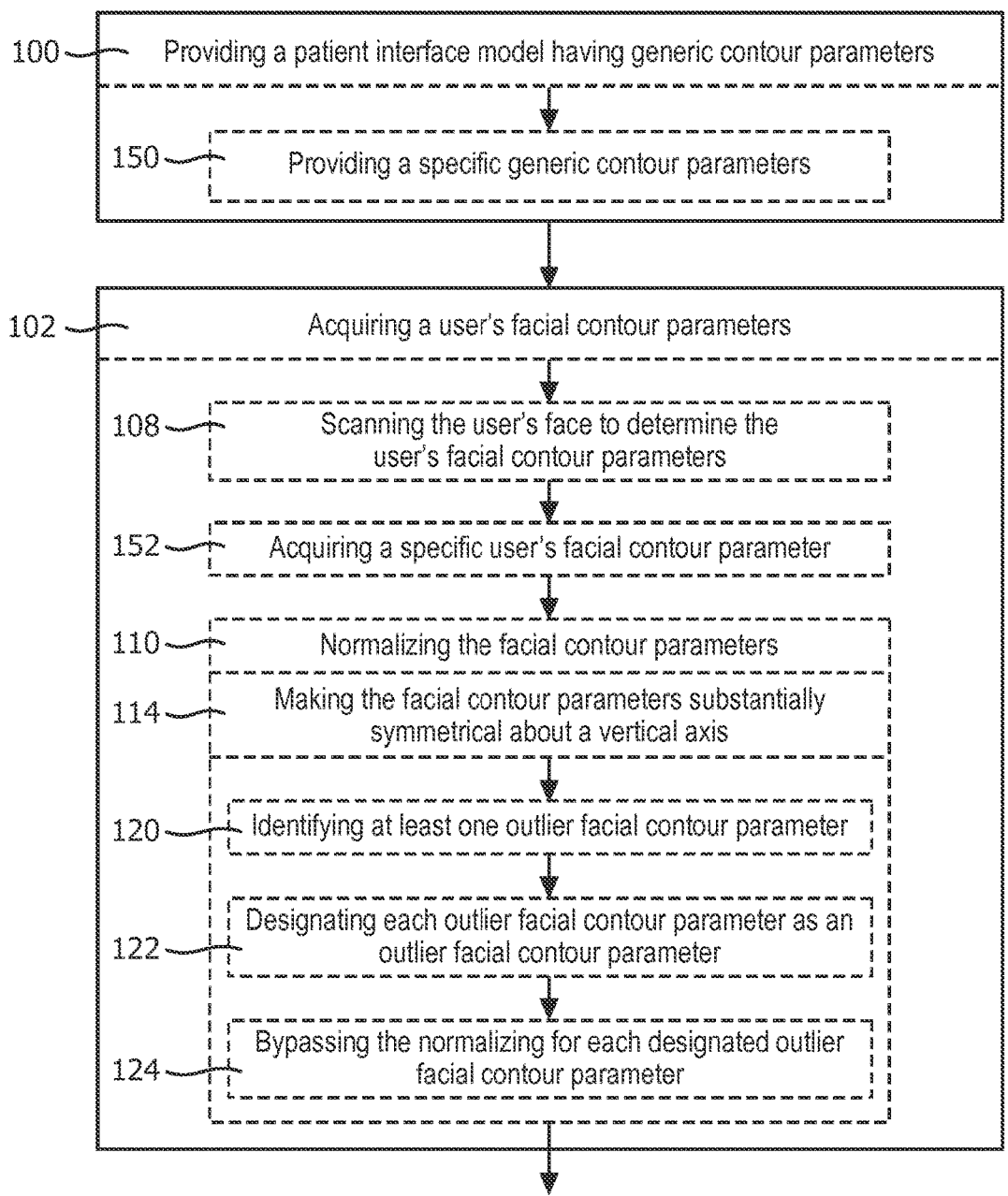
FIGS. 7A and 7B are a flowchart of the steps for the method.
Figure 7B:
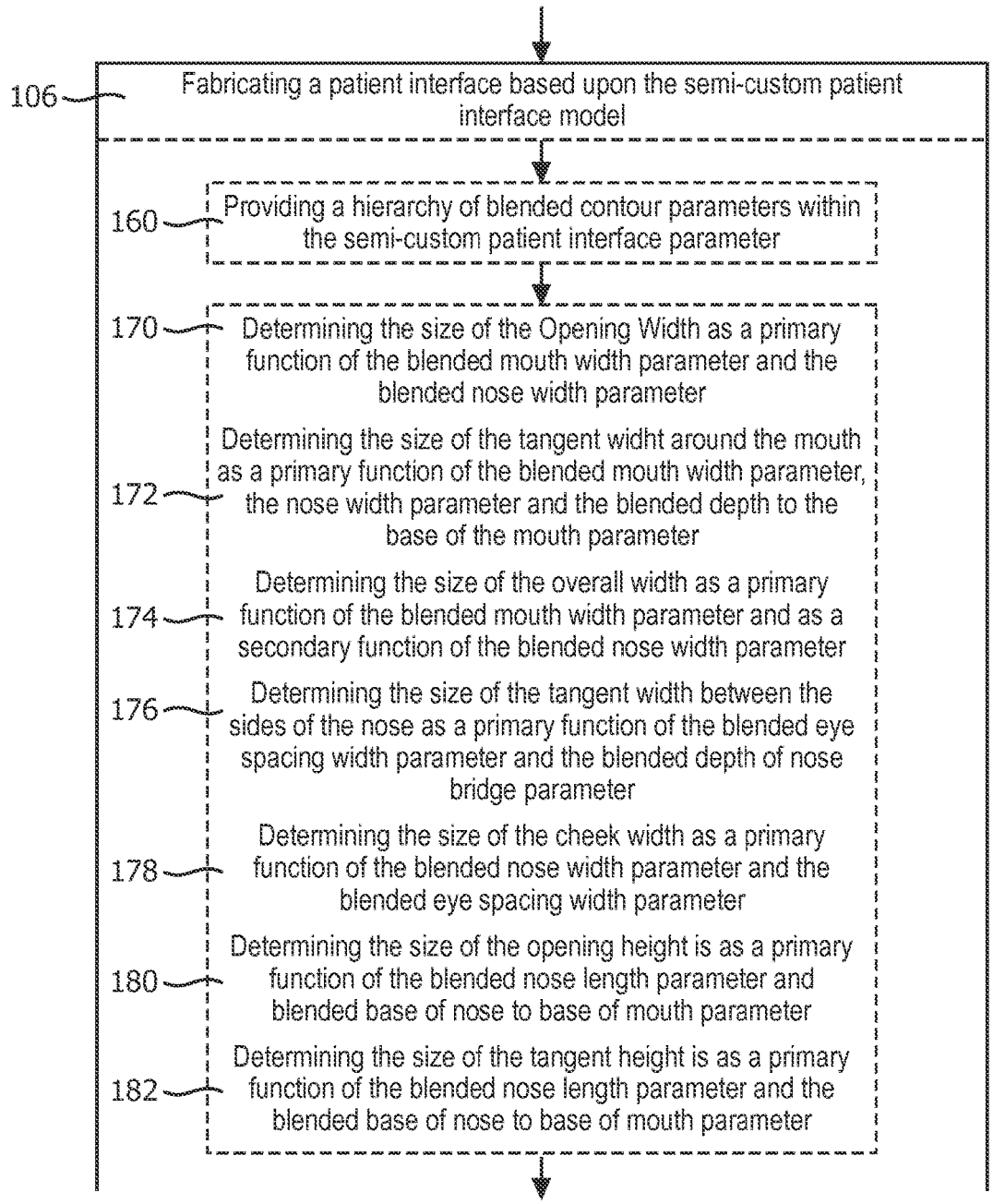

Accordingly, in the exemplary embodiment, a method of providing semi-custom patient interface device 10A, includes a step 100 of providing a patient interface model having generic contour parameters, a step 102 of acquiring a user's facial contour parameters, a step 104 of blending the generic contour parameters and the user's facial contour parameters to create a semi-custom patient interface device parameter set, and, a step 106 of fabricating a semi-custom patient interface device based upon the semi-custom patient interface device parameter set. Furthermore, in the exemplary embodiment, each of the steps 100, 102, 104, and 106 may include a number of sub-steps. Those sub-steps are shown in FIGS. 7A and 7B in dashed boxes in conjunction with each of the main steps 100, 102, 104, and 106. In addition, each of the sub-steps is described in detail below as well as the manner in which they may fit and work together in the exemplary embodiment.

As noted above, laser scanning methods, sonic scanning methods, and imaging methods (e.g., 2D or 3D scanning/mapping) may be used to capture data representing the user's facial features. Thus, the step 102 of acquiring a user's facial contour parameters may include the sub-step 108 of scanning the user's face to determine the user's facial contour parameters.

The step 102 of acquiring a user's facial contour parameters may further include the sub-step 110 of normalizing the user's facial contour parameters. If this step is performed, the step 104 of blending the generic contour parameters and the user's facial contour parameters to create a semi-custom patient interface device parameter set may include the sub-step 112 of blending the generic contour parameters and the normalized user's facial contour parameters to create a semi-custom patient interface device parameter set. The sub-step 110 of normalizing the user's facial contour parameters may include the sub-step 114 of making the horizontal user's facial contour parameters substantially symmetrical about a vertical axis. Further, the sub-step 110 of normalizing user's facial contour parameters may include the sub-step 120 of identifying at least one outlier user's facial contour parameter, the sub-step 122 of designating each outlier user's facial contour parameter as an outlier user's facial contour parameter, and the sub-step 124 of bypassing the normalizing for each designated outlier user's facial contour parameter.

If an outlier user's facial contour parameter is identified 120, then the step 104 of blending the generic contour parameters and the user's facial contour parameters to create a semi-custom patient interface device parameter set may include the sub-step 126 of bypassing the blending of the generic contour parameters and each identified outlier user's facial contour parameter. Finally, each outlier user's facial contour parameter may be incorporated into the semi-custom patient interface device parameter set. That is, the step 104 of blending the generic contour parameters and the user's facial contour parameters to create a semi-custom patient interface device parameter set may include the step 128 of incorporating each outlier user's facial contour parameter into the semi-custom patient interface device parameter set. That is, each outlier user's facial contour parameter is incorporated into the semi-custom patient interface device parameter set without being blended with the associated generic contour parameter.

The step 104 of blending the generic contour parameters and the user's facial contour parameters to create a semi-custom patient interface device parameter set may include the sub-step 130 of providing a weighting factor for at least one of the generic contour parameters or the user's facial contour parameters. When weighted data is used, the step 104 of blending the generic contour parameters and the user's facial contour parameters to create a semi-custom patient interface device parameter set may include the sub-step 132 of blending the at least one of the weighted generic contour parameters or the weighted user's facial contour parameters with the associated contour parameter in the generic contour parameters or user's facial contour parameters.

Based on the foregoing, it can be seen that in an exemplary embodiment of the method, there are steps of providing each of the identified generic parameters, acquiring each of the identified user parameters, providing a weighting factor for each generic and/or user's parameter, and averaging the weighted generic contour parameters and the associated weighted user's facial contour parameters. More specifically, the step 100 of providing a patient interface model having generic contour parameters may include the sub-step 150 of providing a specific generic contour parameter wherein the specific generic contour parameters are selected from the group including a generic Mouth Width parameter, a generic Nose Width parameter, a generic Eye Spacing Width parameter, a generic Nose Length parameter, a generic base of Nose to Base of Mouth parameter, a generic Bridge of Nose to Forehead parameter, a generic Depth of Nose Bridge parameter, a generic Depth to the Base of the Mouth parameter, a generic Right, First Depth to the Side of the Nose parameter, a generic Left, Second Depth to the Side of the Nose parameter, a generic Depth to the Base of the Nose parameter, a generic Right, First Depth to the Corner of the Mouth parameter, a generic Left, Second Depth to the Corner of the Mouth parameter, a generic Right, First Depth to the Base of the Nose parameter, a generic Left, Second Depth to the Base of the Nose parameter, and a generic Depth to the Forehead parameter (as discussed below).

Further, the step 102 of acquiring a user's facial contour parameters includes the sub-step 152 of acquiring a specific user's facial contour parameter wherein the specific user's facial contour parameters are selected from the group including a user's Mouth Width parameter, a user's Nose Width parameter, a user's Eye Spacing Width parameter, a user's Nose Length parameter, a user's base of Nose to Base of Mouth parameter, a user's Bridge of Nose to Forehead parameter, a user's Depth of Nose Bridge parameter, a user's Depth to the Base of the Mouth parameter, a user's Right, First Depth to the Side of the Nose parameter, a user's Left, Second Depth to the Side of the Nose parameter, a user's Depth to the Base of the Nose parameter, a user's Right, First Depth to the Corner of the Mouth parameter, a user's Left, Second Depth to the Corner of the Mouth parameter, a user's Right, First Depth to the Base of the Nose parameter, a user's Left, Second Depth to the Base of the Nose parameter, and a user's Depth to the Forehead parameter (as discussed below).

Further the step 104 of blending the generic contour parameters and the user's facial contour parameters to create a semi-custom patient interface device parameter set may include the sub-step 154 of providing a weighting factor for the specific generic parameters, and/or the sub-step 156 of providing a weighting factor for the specific user's facial contour parameters. The step 104 of blending the generic contour parameters and the user's facial contour parameters to create a semi-custom patient interface device parameter set may include the further sub-step 158 of averaging the weighted specific generic parameters and the weighted specific user's facial contour parameters whereby a set of blended user's facial contour parameters is established. As noted above, the weighting factor may be 0% for any parameter.

The step 106 of fabricating a semi-custom patient interface device 10A based upon the semi-custom patient interface device parameter set may include the sub-step 160 of providing a hierarchy of blended contour parameters within the semi-custom patient interface device parameter set wherein selected blended contour parameters are associated with selected patient interface device dimensions, the hierarchy including at least primary blended contour parameters and secondary blended contour parameters. The blended contour parameters are used to determine the size, shape and contours of semi-custom patient interface device 10A. That is, as noted above, there is a mathematical correlation between the blended contour parameters and the size, shape and contours of final semi-custom patient interface device 10A. The method provides for using only those parameters that have a large influence on the size, shape and contours of final semi-custom patient interface device 10A, i.e. the "primary blended contour parameters," as well as using parameters that have a less influence on the size, shape and contours of final semi-custom patient interface device 10A, i.e. the "secondary blended contour parameters."

Thus, the method, and more specifically the step 106 of fabricating a semi-custom patient interface device 10A based upon the semi-custom patient interface device parameter set, may include the sub-step 162 of creating a model of semi-custom patient interface device wherein the dimensions of the semi-custom patient interface device are calculated as functions of the primary blended contour parameters and secondary blended contour parameters within the semi-custom patient interface device parameter set, and, the sub-step 164 of fabricating semi-custom patient interface device 10A based upon the model of semi-custom patient interface device.

With even more specificity, the sub-step 162 of creating a model of a semi-custom patient interface device wherein the dimensions of the semi-custom patient interface device are calculated as functions of the blended contour parameters within the semi-custom patient interface device parameter set may include the sub-step 170 of determining the size of the Opening Width as a primary function of the blended Mouth Width parameter and the blended Nose Width parameter and as a secondary function of the blended Right, First Depth to the Corner of the Mouth parameter and the secondary blended Left, Second Depth to the Corner of the Mouth parameter; the sub-step 172 of determining the size of the Tangent Width around the Mouth as a primary function of the blended Mouth Width parameter, the blended Nose Width parameter, and the blended Depth to the Base of the Mouth parameter and as a secondary function of the blended Right, First Depth to the Corner of the Mouth parameter and the blended Left, Second Depth to the corner of the Mouth parameter; the sub-step 174 of determining the size of the Overall Width as a primary function of the blended Mouth Width parameter and as a secondary function of the blended Nose Width parameter; the sub-step 176 of determining the size of the Tangent Width between the Sides of the Nose as a primary function of the blended Eye Spacing Width parameter and the blended Depth of Nose Bridge parameter and as a secondary function of the blended Right, First Depth to the Side of the Nose parameter and the blended Left, Second Depth to the Side of the Nose parameter; the sub-step 178 of determining the size of the Cheek Width as a primary function of the blended Nose Width parameter and the blended Eye Spacing Width parameter and as a secondary function of the blended Nose Length parameter, the blended Right, First Depth to the Side of the Nose parameter, the blended Left, Second Depth to the Side of the Nose parameter, the secondary blended Right, First Depth to the Base of the Nose parameter, and the blended Left, Second Depth to the Base of the Nose parameter; the sub-step 180 of determining the size of the Opening Height is as a primary function of the blended Nose Length parameter and the blended Base of Nose to Base of Mouth parameter; and, the sub-step 182 of determining the size of the Tangent Height is as a primary function of the blended Nose Length parameter and the blended Base of Nose to Base of Mouth parameter and as a secondary function of the blended Depth of Nose Bridge parameter and the blended Depth to the Base of the Mouth parameter. Alternatively, the secondary functions may be ignored and the characteristics of the model may be based on the primary functions exclusively.

It is noted that the model may be presented as a three dimensional image. This may aid in identifying defects or problems with the model prior to fabrication. Thus, the sub-step 162 of creating a model of semi-custom patient interface device 10A wherein the dimensions of the semi-custom patient interface device 10A are calculated as functions of the primary blended contour parameters and secondary blended contour parameters within the semi-custom patient interface device parameter set may include the further sub-step 190 of generating a three dimensional model of semi-custom patient interface device, and, the sub-step 192 of displaying the three dimensional model of semi-custom patient interface device.

Figure 8:
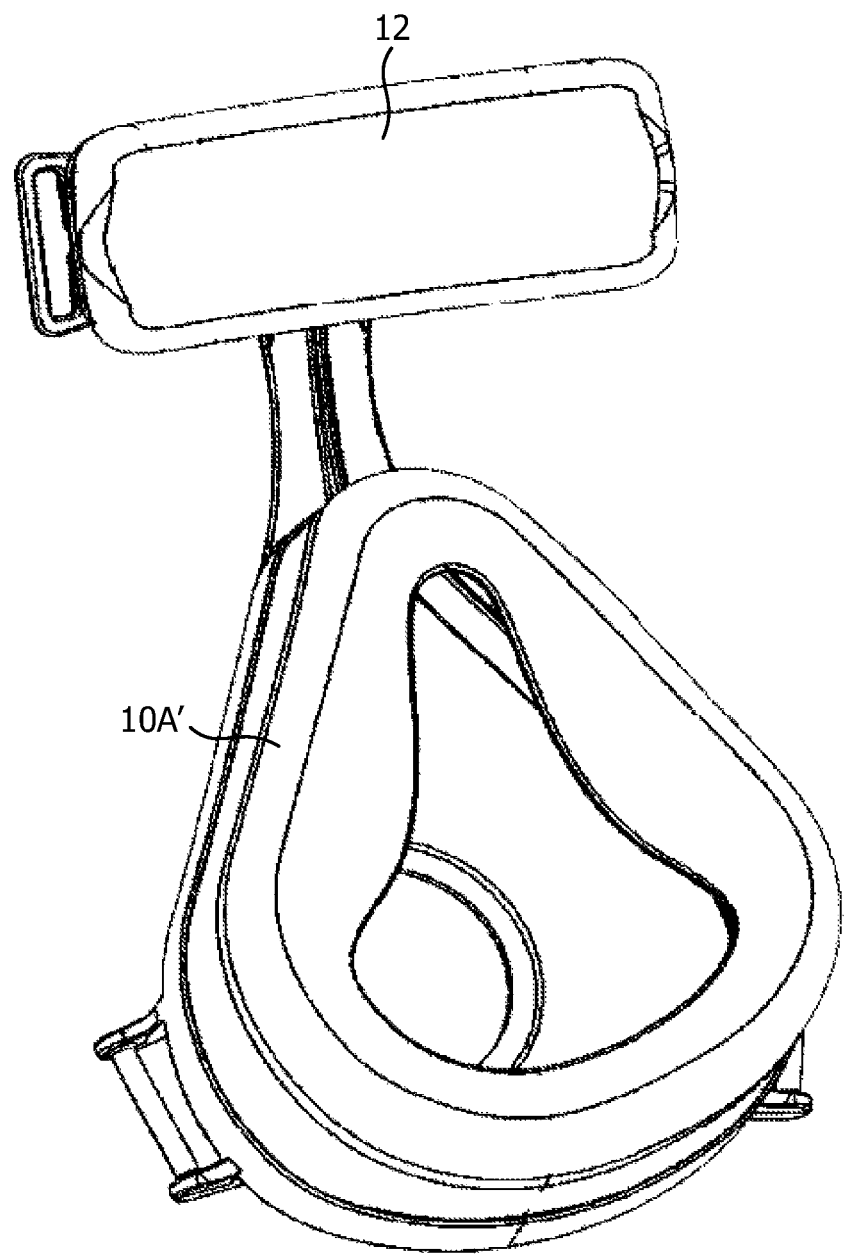
FIG. 8 is an isometric view of an alternate semi-custom patient interface device.

As shown in FIG. 8, some semi-custom patient interface devices 10A' include a forehead pad 12, thus having the identifiable dimension of a Forehead Pad Height. Alternate semi-custom patient interface devices 10A' may also include a semi-custom Forehead Pad Height dimension. In this exemplary embodiment, the specific generic contour parameters include a generic Depth to the Forehead parameter. Thus, there is a corresponding specific user's facial contour parameter, namely user's Depth to the Forehead parameter. As with the other generic parameters and user's facial contour parameters, the generic Depth to the Forehead parameter and the user's Depth to the Forehead parameter may be weighted and blended as discussed above. In this exemplary embodiment, the step 106 of fabricating a semi-custom patient interface device based upon the semi-custom patient interface device parameter set include the additional sub-step 184 of determining the Forehead Pad Height as a function of the blended Depth to the Forehead parameter.

Figure 9:
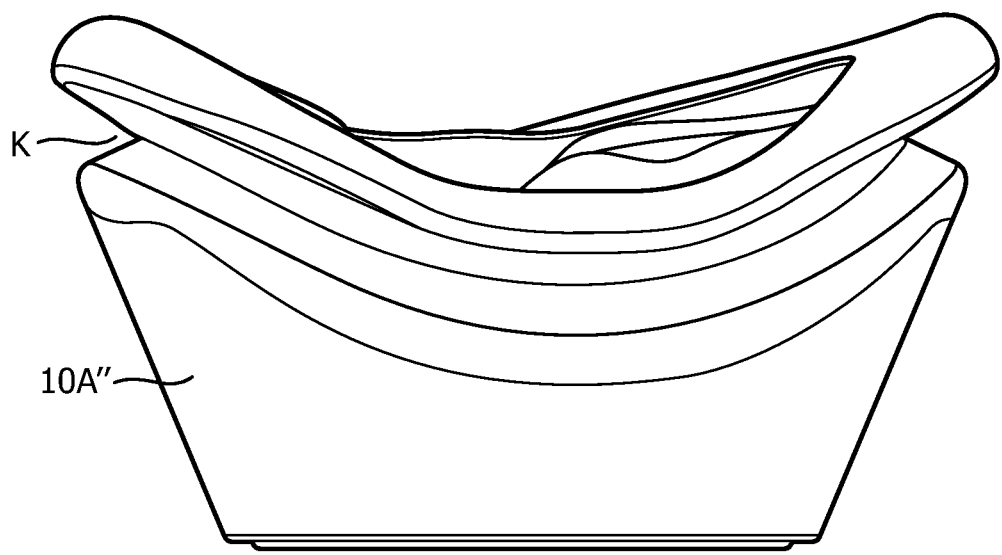
FIG. 9 is an isometric view of an alternate semi-custom patient interface device.

As shown in FIG. 9, some patient interface devices 10A" include a pleated cushion 14, thus having the identifiable dimension of a Minimum Groove Depth K. With this configuration, the step 106 of fabricating a patient interface based upon the semi-custom patient interface device parameter set includes the additional sub-step 186 of determining the depth of the groove in the patient interface is a primary function of the blended Eye Spacing Width parameter.

Further it is noted that, because the object of this invention is to create semi-custom patient interface device 10A, the dimensions of patient interface device 10 should not be based exclusively on the user's facial contour parameters. Thus, the step 106 of fabricating a patient interface based upon the semi-custom patient interface device parameter set may be said to include the sub-step 240 of not fabricating the patient interface based exclusively upon the user's facial contour parameters.

The embodiment set forth above utilizes a specific set of parameters set forth above. The method, however, is not limited to this single set of parameters and other sets of parameters, including parameters that are not identifies above, could be used in association with this method.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by on and the same item of hardware. The word "a" or "an" preceding an element does not exclude the presence of a plurality of such elements. In any device claim enumerating several means, several of these means may be embodied by one and the same item of hardware The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of creating a semi-custom patient interface device, the method comprising the steps of:
    providing a patient interface model having a set of generic contour parameters;
    acquiring a set of user's facial contour parameters from a user including normalizing one or more of the user's facial contour parameters;
    blending the generic contour parameters and the user's facial contour parameters to create a semi-custom patient interface device parameter set including blending one or more of the generic contour parameters and the normalized user's facial contour parameters during the creation of the semi-custom patient interface device parameter set; and
    fabricating the semi-custom patient interface device based upon the semi-custom patient interface device parameter set, wherein the user's facial contour parameters include a number of horizontal user's facial contour parameters, and wherein the step of normalizing one or more of the user's facial contour parameters includes:
    making a user's horizontal user's facial contour parameters substantially symmetrical about a vertical axis.

2. A method of creating a semi-custom patient interface device, the method comprising the steps of:
    providing a patient interface model having a set of generic contour parameters;
    acquiring a set of user's facial contour parameters from a user including normalizing one or more of the user's facial contour parameters;
    blending the generic contour parameters and the user's facial contour parameters to create a semi-custom patient interface device parameter set including blending one or more of the generic contour parameters and the normalized user's facial contour parameters during the creation of the semi-custom patient interface device parameter set; and
    fabricating the semi-custom patient interface device based upon the semi-custom patient interface device parameter set;
    wherein the step of normalizing the user's facial contour parameters includes:
        identifying an outlier user's facial contour parameter from the set of user's facial contour parameters;
        designating the outlier user's facial contour parameter as an outlier user's facial contour parameter; and
        bypassing the normalizing for the designated outlier user's facial contour parameter.

3. The method of claim 2, wherein the step of blending the generic contour parameters and the normalized user's facial contour parameters to create the semi-custom patient interface device parameter set includes:
    blending one of more of the generic contour parameters and the normalized user's facial contour parameters to create a partial semi-custom patient interface device parameter set; and
    incorporating the outlier user's facial contour parameter into the partial semi-custom patient interface device parameter set to form the semi-custom patient interface device parameter set.

4. A method of creating a semi-custom patient interface device, the method comprising the steps of:
    providing a patient interface model having a set of generic contour parameters;
    acquiring a set of user's facial contour parameters from a user including normalizing one or more of the user's facial contour parameters;

blending the generic contour parameters and the user's facial contour parameters to create a semi-custom patient interface device parameter set including blending one or more of the generic contour parameters and the normalized user's facial contour parameters during the creation of the semi-custom patient interface device parameter set; and fabricating the semi-custom patient interface device based upon the semi-custom patient interface device parameter set, wherein the step of blending the generic contour parameters and the normalized user's facial contour parameters to create the semi-custom patient interface device parameter set includes:

weighting one of the generic contour parameters or the user's facial contour parameters using a weighting factor to create a weighted parameter; and wherein the blending includes blending the weighted parameter with: (i) one of the generic contour parameters if the weighted parameter is based on the user's facial contour parameters, or, (ii) one of the user's facial contour parameters if the weighted contour parameter is based on the generic contour parameters.

5. A method of creating a semi-custom patient interface device, wherein semi-custom patient interface device has identifiable dimensions including Opening Width, Tangent Width around Mouth, Overall Width, Tangent Width between the Sides of the Nose, Cheek Width, Opening Height, and, Tangent Height, the method comprising the steps of:

providing a patient interface model having a set of generic contour parameters;

acquiring a set of user's facial contour parameters from a user;

blending the generic contour parameters and the user's facial contour parameters to create a semi-custom patient interface device parameter set;

creating a model of the semi-custom patient interface device wherein the dimensions of the semi-custom patient interface device are calculated as functions of the blended contour parameters within the semi-custom patient interface device parameter set;

determining the size of the Opening Width as a primary function of a blended Mouth Width parameter and a blended Nose Width parameter;

determining the size of a Tangent Width around Mouth as a primary function of a blended Mouth Width parameter, a blended Nose Width parameter, and a blended Depth to the Base of the Mouth parameter; determining the size of the Overall Width as a primary function of a blended Mouth Width parameter; determining the size of the Tangent Width between the Sides of the Nose as a primary function of a blended Eye Spacing Width parameter and a blended Depth of Nose Bridge parameter;

determining the size of the Cheek Width as a primary function of a blended Nose Width parameter and a blended Eye Spacing Width parameter;

determining the size of the Opening Height is as a primary function of a blended Nose Length parameter and a blended Base of Nose to Base of Mouth parameter;

determining the size of the Tangent Height is as a primary function of a blended Nose Length parameter and a blended Base of Nose to Base of Mouth parameter;

fabricating the semi-custom patient interface device based upon the semi-custom patient interface device parameter set; and fabricating the semi-custom patient interface device based upon the model of the semi-custom patient interface device.

6. A method of creating a semi-custom patient interface device, the method comprising the steps of:

providing a patient interface model having a set of generic contour parameters;

providing a specific generic contour parameter wherein the specific generic contour parameters are selected from the group including a generic Mouth Width parameter, a generic Nose Width parameter, a generic Eye Spacing Width parameter, a generic Nose Length parameter, a generic base of Nose to Base of Mouth parameter, a generic Bridge of Nose to Forehead parameter, a generic Depth of Nose Bridge parameter, a generic Depth to the Base of the Mouth parameter, a generic Right, First Depth to the Side of the Nose parameter, a generic Left, Second Depth to the Side of the Nose parameter, a generic Depth to the Base of the Nose parameter, a generic Right, First Depth to the Corner of the Mouth parameter, a generic Left, Second Depth to the Corner of the Mouth parameter, a generic Right, First Depth to the Base of the Nose parameter, and a generic Left, Second Depth to the Base of the Nose parameter;

acquiring a set of user's facial contour parameters from a user;

acquiring a specific user's facial contour parameter wherein the specific user's facial contour parameters are selected from the group including a user's Mouth Width parameter, a user's Nose Width parameter, a user's Eye Spacing Width parameter, a user's Nose Length parameter, a user's base of Nose to Base of Mouth parameter, a user's Bridge of Nose to Forehead parameter, a user's Depth of Nose Bridge parameter, a user's Depth to the Base of the Mouth parameter, a user's Right First Depth to the Side of the Nose parameter, a user's Left, Second Depth to the Side of the Nose parameter, a user's Depth to the Base of the Nose parameter, a user's Right, First Depth to the Corner of the Mouth parameter, a user's Left, Second Depth to the corner of the Mouth parameter, a user's Right, First Depth to the Base of the Nose parameter, and a user's Left, Second Depth to the Base of the Nose parameter;

blending the generic contour parameters and the user's facial contour parameters to create a semi-custom patient interface device parameter set; and fabricating the semi-custom patient interface device based upon the semi-custom patient interface device parameter set;

wherein the step of fabricating the semi-custom patient interface device based upon the semi-custom patient interface device parameter set includes:

providing a hierarchy of blended contour parameters within the semi-custom patient interface device parameter set wherein selected blended contour parameters are associated with selected patient interface device dimensions, the hierarchy including at least primary blended contour parameters and secondary blended contour parameters, creating a model of a semi-custom patient interface device wherein the dimensions of the semi-custom patient interface device are calculated as functions of the primary blended contour parameters and secondary blended contour parameters within the semi-custom patient interface device parameter set; and fabricating a semi-custom patient interface device based upon the model of a semi-custom patient interface device;

wherein the semi-custom patient interface device has identifiable dimensions including Opening Width, Tangent Width around Mouth, Overall Width, Tangent Width between the Sides of the Nose, Cheek Width, Opening Height, and, Tangent Height, and wherein the step of creating a model of semi-custom patient interface device wherein the dimensions of semi-custom patient interface device are calculated as functions of the blended contour parameters within the semi-custom patient interface device parameter set includes:

determining the size of the Opening Width as a primary function of a blended Mouth Width parameter and a blended Nose Width parameter and as a secondary function of a blended Right, First Depth to the Corner of the Mouth parameter and a blended Left, Second Depth to the corner of the Mouth parameter;

determining the size of the Tangent Width around Mouth as a primary function of a blended Mouth Width parameter, a blended Nose Width parameter, and a blended Depth to the Base of the Mouth parameter and as a secondary function of a blended Right, First Depth to the Corner of the Mouth parameter and a blended Left, Second Depth to the Corner of the Mouth parameter;

determining the size of the Overall Width as a primary function of a blended Mouth Width parameter and as a secondary function of a blended Nose Width parameter;

determining the size of the Tangent Width between the Sides of the Nose as a primary function of a blended Eye Spacing Width parameter and a blended Depth of Nose Bridge parameter and as a secondary function of a blended Right, First Depth to the Side of the Nose parameter and a blended Left, Second Depth to the Side of the Nose parameter;

determining the size of the Cheek Width as a primary function of a blended Nose Width parameter and a blended Eye Spacing Width parameter and as a secondary function of a blended Nose Length parameter, a blended Right, First Depth to the Side of the Nose parameter, a blended Left, Second Depth to the Side of the Nose parameter, a blended Right, First Depth to the Base of the Nose parameter, and a blended Left, Second Depth to the Base of the Nose parameter;

determining the size of the Opening Height is as a primary function of a blended Nose Length parameter and a blended Base of Nose to Base of Mouth parameter; and determining the size of the Tangent Height is as a primary function of a blended Nose Length parameter and a blended Base of Nose to Base of Mouth parameter and as a secondary function of a blended Depth of Nose Bridge parameter and a blended Depth to the Base of the Mouth parameter.

7. A method of creating a semi-custom patient interface device, wherein the semi-custom patient interface device includes a forehead pad and the identifiable dimension of a Forehead Pad Height, the method comprising the steps of:

providing a patient interface model having a set of generic contour parameters;

providing a generic Depth to the Forehead parameter;

acquiring a set of user's facial contour parameters from a user;

acquiring a user's Depth to the Forehead parameter;

blending the generic contour parameters and the user's facial contour parameters to create a semi-custom patient interface device parameter set;

providing a weighting factor for the generic Depth to the Forehead parameter;

providing a weighting factor for the user's Depth to the Forehead parameter;

averaging the weighted generic Depth to the Forehead parameter and the weighted user's Depth to the Forehead parameters whereby a blended Depth to the Forehead parameter is established;

fabricating the semi-custom patient interface device based upon the semi-custom patient interface device parameter set; and fabricating a semi-custom patient interface device wherein the size of the forehead pad height is a function of the blended Depth to the Forehead parameter.

8. A method of creating a semi-custom patient interface device, wherein semi-custom patient interface device includes a pleated cushion and an identifiable dimension of a minimum groove depth, the method comprising the steps of:

providing a patient interface model having a set of generic contour parameters;

acquiring a set of user's facial contour parameters from a user;

blending the generic contour parameters and the user's facial contour parameters to create a semi-custom patient interface device parameter set;

fabricating the semi-custom patient interface device based upon the semi-custom patient interface device parameter set; and fabricating a semi-custom patient interface wherein a Depth of the Groove in the patient interface is a primary function of a blended Eye Spacing width parameter.

* * * * *